United States Patent
Hicks et al.

(10) Patent No.: US 10,626,084 B2
(45) Date of Patent: Apr. 21, 2020

(54) METHOD FOR PRODUCING TWO ISOCYANATES

(71) Applicant: COVESTRO LLC, Pittsburgh, PA (US)

(72) Inventors: Amber Hicks, Pearland, TX (US);
Kevin Kelleher, Houston, TX (US);
William Hassell, Seabrook, TX (US);
Wingwah Lau, Houston, TX (US)

(73) Assignee: Covestro LLC, Pittsburgh, PA (US)

( * ) Notice: Subject to any disclaimer, the term of this patent is extended or adjusted under 35 U.S.C. 154(b) by 32 days.

(21) Appl. No.: 16/054,335

(22) Filed: Aug. 3, 2018

(65) Prior Publication Data

US 2020/0039925 A1 Feb. 6, 2020

(51) Int. Cl.
*C07C 263/10* (2006.01)
*C07C 263/04* (2006.01)
*B01D 3/34* (2006.01)
*B01D 3/14* (2006.01)

(52) U.S. Cl.
CPC .............. *C07C 263/10* (2013.01); *B01D 3/14* (2013.01); *B01D 3/34* (2013.01); *C07C 263/04* (2013.01)

(58) Field of Classification Search
CPC ....... C07C 263/10; C07C 263/04; B01D 3/34; B01D 3/14
See application file for complete search history.

(56) References Cited

U.S. PATENT DOCUMENTS

| | | | |
|---|---|---|---|
| 2,764,607 A | 9/1956 | Hieserman et al. | |
| 3,234,253 A * | 2/1966 | Cooper et al. | C07C 263/10 560/347 |
| 3,544,611 A | 12/1970 | Michelet et al. | |
| 5,449,818 A | 9/1995 | Biskup et al. | |
| 5,633,396 A | 5/1997 | Bischof et al. | |
| 6,800,781 B2 | 10/2004 | Herold et al. | |
| 7,118,653 B2 | 10/2006 | Brady et al. | |
| 7,584,629 B2 | 9/2009 | Sohn et al. | |
| 7,645,900 B2 | 1/2010 | Lorenz et al. | |
| 7,915,444 B2 | 3/2011 | Wolfert et al. | |
| 8,288,584 B2 * | 10/2012 | Knoesche | C07C 263/10 560/341 |
| 8,563,768 B2 | 10/2013 | Bruins et al. | |
| 8,692,016 B2 | 4/2014 | Sanders et al. | |
| 9,024,057 B2 | 5/2015 | Biskup et al. | |
| 2010/0041915 A1 | 2/2010 | Woelfert et al. | |
| 2018/0194720 A1 | 7/2018 | Steffens et al. | |

FOREIGN PATENT DOCUMENTS

| | | |
|---|---|---|
| DE | 100 27 779 A1 | 12/2001 |
| GB | 737 442 A | 9/1955 |

OTHER PUBLICATIONS

Kister, Henry Z., Distillation Operation, McGraw Hill Professional, Ch. 17.2, 1990 (abstract).
Chemie Ingenieur Technik, vol. 44 (18): 1051-1056, Sep. 1972 (abstract).
Branan, Carl R., Process Evaluation—What Size Should a Plant Be?, Rules of Thumb for Chemical Engineers, 4th ed, p. 240-273, 2005 (abstract).
Weinhem, Chemical Plant Design and Construction, Ullmann's Encyclopedia of Industrial Chemistry, vol. 8: 273, 2012.

* cited by examiner

*Primary Examiner* — Paul A Zucker
(74) *Attorney, Agent, or Firm* — Richard P. Bender

(57) ABSTRACT

A method and a continuous process for producing two isocyanates by reacting a first amine with phosgene in a stoichiometric excess in the gas phase to produce a first isocyanate. The excess phosgene is subsequently recovered and recirculated back to react with a second amine to produce a second isocyanate. In an embodiment, both fresh and recycled phosgene may be used in reacting each respective amine to produce an isocyanate. The amine streams contain two different concentrations of hydrogen chloride: one may be between 0.0 and 0.1%, and another may be between 1 and 5% by weight.

16 Claims, 2 Drawing Sheets

US 10,626,084 B2

METHOD FOR PRODUCING TWO ISOCYANATES

FIELD

The invention relates to a process for preparing two isocyanates by reaction of a first amine with freshly generated phosgene, while a second amine is reacted with phosgene that is recovered from a distillation column downstream of the reaction of both amines.

SUMMARY OF THE INVENTION

The present invention provides a continuous process for preparing a first isocyanate by gas phase phosgenation of a first amine, and a second isocyanate by gas phase phosgenation of a second amine, comprising (i) reacting the first amine with freshly generated phosgene to obtain a first process product; (ii) treating the first process product with a first solvent at a temperature which is below the boiling point of the first isocyanate to give a gaseous stream (ii-1) containing hydrogen chloride and unreacted phosgene and a liquid stream (ii-2) containing the first solvent and the first isocyanate; (iii) feeding stream (ii-1) to a distillation column (iii) to give a liquid phosgene-containing stream (iii-1) and a gaseous stream (iii-2) containing hydrogen chloride; (iv) introducing stream (iii-1) to a distillation column (iv), from which a gaseous phosgene-containing stream (iv) is taken off at the top; (v) reacting the second amine with an excess of phosgene that comprises gaseous phosgene-containing stream (iv) to obtain a second process product; (vi) treating the second process product with a second solvent at a temperature which is below the boiling point of the second isocyanate to give a gaseous stream (vi-1) containing hydrogen chloride and unreacted phosgene and a liquid stream (vi-2) containing the second solvent and the second isocyanate; (vii) feeding stream (vi-1) to distillation column (iii); (viii) working up the liquid stream (ii-2) containing solvent and the first isocyanate to isolate the first isocyanate; (ix) working up the liquid stream (vi-2) containing solvent and the second isocyanate to isolate the second isocyanate.

Another embodiment of the invention provides a continuous process for preparing a first isocyanate by gas phase phosgenation of a first amine, and a second isocyanate by gas phase phosgenation of a second amine, comprising: (i) reacting the first amine with an excess of phosgene having a concentration of hydrogen chloride of HCl-1 to obtain a first process product; (ii) treating the first process product with a first solvent at a temperature which is below the boiling point of the first isocyanate to give a gaseous stream (ii-1) containing hydrogen chloride and unreacted phosgene and a liquid stream (ii-2) containing the first solvent and the first isocyanate; (iii) feeding stream (ii-1) to a distillation column (iii) to give a liquid phosgene-containing stream (iii-1) and a gaseous stream (iii-2) containing hydrogen chloride; (iv) introducing stream (iii-1) to a distillation column, from which a gaseous phosgene-containing stream (iv) is taken off at the top; (v) splitting the gaseous phosgene-containing stream (iv) into stream (v-1) and stream (v-2); (vi) recirculating stream (v-1) to step (i); (vii) working up the liquid stream (ii-2) containing the first solvent and the first isocyanate to isolate the first isocyanate; (viii) reacting the second amine with an excess of phosgene having a concentration of hydrogen chloride of HCl-2 to obtain a second process product; (ix) treating the second process product with a second solvent at a temperature which is below the boiling point of the second isocyanate to give a gaseous stream (ix-1) containing hydrogen chloride and unreacted phosgene and a liquid stream (ix-2) containing the second solvent and the second isocyanate; (x) feeding stream (ix-1) to distillation column (iii); (xi) recirculating stream (v-2) to step (viii); (xii) working up the liquid stream (ix-2) containing the second solvent and the second isocyanate to isolate the second isocyanate, wherein the excess of phosgene in step (i) comes at least partially from stream (v-1), wherein the excess of phosgene in step (viii) comes at least partially from stream (v-2), wherein HCl-2 is greater than HCl-1.

In other embodiments, the first amine in step (i) is not reacted with any recycled phosgene, while in other embodiments, recycled phosgene is added. In still other embodiments, the second amine is reacted with both fresh and recycled phosgene, while in others, only recycled phosgene is used.

In still another embodiment of the present invention, the phosgene that is reacted with the first amine has a concentration of hydrogen chloride HCl-1 and the phosgene that is reacted with the second amine has a concentration of hydrogen chloride HCl-2, and wherein HCl-2 is greater than HCl-1. In another embodiment, HCl-1 is between 0.0% and 0.1% by weight. In yet another embodiment, HCl-2 is between 1% and 5% by weight.

In a different embodiment, the first process product has a corresponding carbamoyl chloride and the temperature of the first quench step is above the decomposition temperature of the corresponding carbamoyl chloride. In still another embodiment, the second process product has a corresponding carbamoyl chloride and the temperature of the second quench step is above the decomposition temperature of the corresponding carbamoyl chloride. In another embodiment, the first solvent is the same as the second solvent.

DETAILED DESCRIPTION

Isocyanates are produced in large quantities and serve mainly as starting materials for the preparation of polyurethanes. They are usually prepared by reaction of the corresponding amines with phosgene, with phosgene being used in a stoichiometric excess. In these syntheses, the excess phosgene may be recovered through distillation, and then recycled, or recirculated, back to the reaction with the amine. However, by-product hydrogen chloride is also created from the reaction. It may be separated from the recovered phosgene, so that phosgene with a low concentration of hydrogen chloride may be used in the reaction. Alternatively, recovered excess phosgene may be destroyed and disposed of safely, if it cannot be used in the reaction.

In the processes of the present invention, two isocyanates are produced from two amines, where the concentration of hydrogen chloride in the phosgene is greater in the reaction of the second amine than in the phosgene used in the reaction of the first amine.

Figure 1:
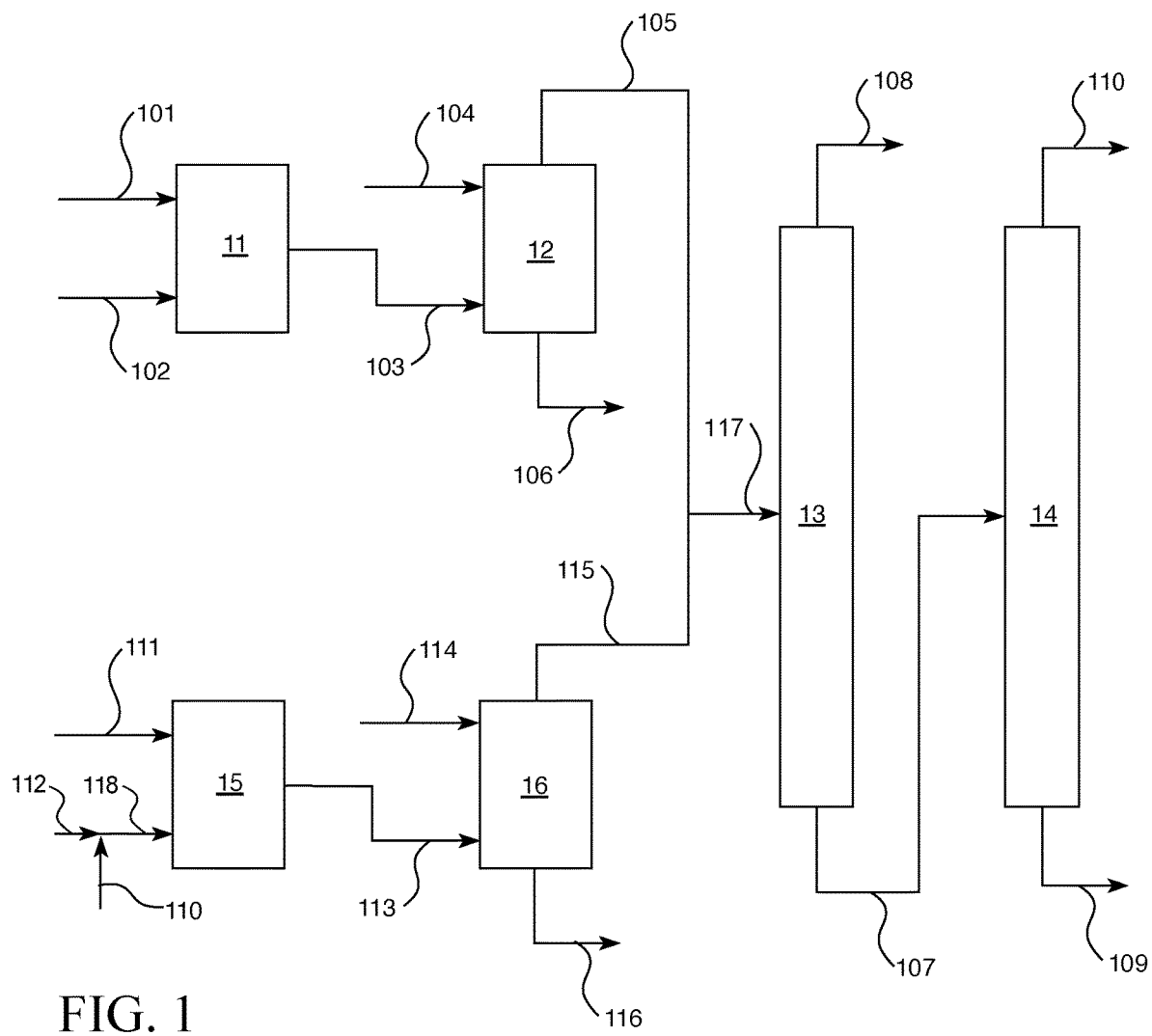
FIG. 1 is a process flow diagram of a continuous process of an embodiment the present invention.

Referring now to the drawings, as shown in FIG. 1, a first amine is carried through stream 101 to be reacted with freshly generated phosgene in stream 102 in reactor 11, to create a first process product in stream 103. In an embodiment of the present invention, only freshly generated phosgene is present in stream 102, in addition to any optional inert or carrier gases, and no recycled phosgene is present in stream 102. The concentration of hydrogen chloride (HCl) in stream 102 is between 0.0% and 0.1%. In an embodiment, it is between greater than 0.0% and 0.1%.

Here, it is possible to use either aliphatic or aromatic monoamines and polyamines. Examples of preferred aromatic amines are toluenediamine (TDA), in particular 2,4-TDA and 2,6-TDA and mixtures thereof, diaminobenzene, naphthalenediamine (NDA) and 2,2'-, 2,4'- or 4,4'-methylenedi(phenylamine) (MDA) or isomer mixtures thereof.

Furthermore, amines, in particular diamines, based on aliphatic or cycloaliphatic hydrocarbons having from 2 to 18 carbon atoms are particularly suitable. Particularly well-suited amines are 1,6-diaminohexane (HMDA), 1-amino-3,3,5-trimethyl-5-aminomethylcyclohexane (IPDA), 1,5-diaminopentane, m-xylylenediamine, and 4,4'-diaminodicyclohexylamine.

The starting amines are generally vaporized and heated to from 200° C. to 600° C., preferably from 200° C. to 500° C., particularly preferably from 250° C. to 450° C., and optionally diluted with an inert gas such as $N_2$, He, Ar or with vapors of an inert solvent, e.g. aromatic hydrocarbons, optionally with halogen substitution, e.g. chlorobenzene or o-dichlorobenzene, before introduction into the reaction space before carrying out the process of the invention.

The vaporization of the starting amines can be carried out in all known vaporization apparatuses, with preference being given to vaporization systems in which a small working content is conveyed at a high circulation rate through a falling film evaporator; to minimize the thermal stress on the starting amines, the vaporization operation can, as indicated above, optionally be assisted by introduction of inert gas and/or vapors of an inert solvent. As an alternative, the vaporization can also be carried out in a vaporization apparatus.

In the process, phosgene is used in an excess over the amine groups to be reacted. A molar ratio of phosgene to amine groups of from 1.1 to 20, preferably from 1.2 to 5, is preferably present. The phosgene, too, is heated to temperatures of from 200° C. to 600° C. and optionally diluted with an inert gas such as $N_2$, He, Ar or with vapors of an inert solvent, e.g. aromatic hydrocarbons without or with halogen substitution, e.g. chlorobenzene or o-dichlorobenzene, before being fed into the reaction space.

The process of the invention in reactor 11 is preferably carried out in such a way that the separately heated reactants in streams 101 and 102 are introduced via at least one mixing device into at least one reaction space, mixed and reacted under preferably adiabatic reaction conditions, ensuring suitable reaction times. The isocyanate in the first process product is subsequently condensed by cooling of the gas stream, with cooling being carried out to a temperature above the decomposition temperature of the corresponding carbamoyl chloride, i.e., for example, 1,6-diaminohexane acid chloride and 1,6-diaminohexane bis-acid chloride in the case of HMDA.

The residence time necessary for reaction of the amine groups with the phosgene to form isocyanate is in the range from 0.05 to 15 seconds, depending on the type of amine used, the initial temperature, the adiabatic temperature increase in the reaction space, the molar ratio of amine used and phosgene, any dilution of the reactants with inert gases and also the reaction pressure selected.

In this step, particular preference is given to using reactors having essentially rotationally symmetric reaction spaces, in which the gaseous starting materials, optionally diluted with inerts, are fed into the at least one mixing space according to the jet mixer principle (Chemie-Ing. Techn. 44 (1972) page 1055, FIG. 10).

Preference is given to neither the reaction space nor any mixing apparatuses or mixing spaces having heating surfaces which could give rise to thermal stressing with the consequence of subsequent reactions such as isocyanurate or carbodiimide formation or cooling surfaces which can give rise to condensation with the consequence of deposits. The components are thus, disregarding any radiation and conduction losses, preferably reacted adiabatically, with the adiabatic temperature increase in mixing apparatus and reactor or reactor alone being established by means of the temperatures, compositions and relative amounts of the feed streams and also the residence time in the mixing apparatuses and the reactors. A nonadiabatic reaction of the components is also possible in the process of the invention.

After the phosgenation reaction has occurred in reactor 11, the first process product, which comprises the isocyanate formed, phosgene and hydrogen chloride, is carried through stream 103 to quench 12, where the first process product is treated with a solvent, which stops any further reaction and separates the isocyanate formed from the gaseous phosgene and hydrogen chloride.

As shown in FIG. 1, the first process product which continuously leaves reactor 11 is condensed with an inert solvent in quench 12. The condensation is preferably carried out by the process product leaving reactor 11 being conveyed in stream 103 into quench 12 into which one or more suitable solvent streams, or quenching liquids, comprising a first solvent are sprayed, shown as stream 104. Rapid cooling of the gas mixtures without the use of cold surfaces can be carried out thereby, as described in EP-A-1 403 248.

The treatment with solvent is carried out at a temperature which is below the boiling point of the isocyanate and above the decomposition temperature of the corresponding carbamoyl chloride, so as to give a gaseous stream (ii-1) containing hydrogen chloride and unreacted phosgene, shown in stream 105 and a liquid stream (ii-2) containing solvent and isocyanate, shown in stream 106. To isolate the isocyanate selectively from the gaseous reaction mixture, solvent such as chlorobenzene and/or dichlorobenzene maintained at a temperature of from 80° C. to 200° C., preferably from 80° C. to 180° C., or isocyanate or mixtures of the isocyanate with chlorobenzene and/or dichlorobenzene kept in these temperature ranges are particularly well-suited. The proportion by mass of the isocyanate which condenses in quench 12 or goes through quench 12 in uncondensed form from the physical data at a given temperature, pressure and composition may be calculated. Likewise, the proportion by mass of the excess phosgene, hydrogen chloride and inert gas optionally used as diluent which goes through quench 12 in uncondensed form or dissolves in the quenching liquid, may also be calculated.

The gas mixture (ii-1) leaving the condensation or quenching stage, shown in stream 105, may be optionally treated to remove residual isocyanate by means of a suitable scrubbing liquid in a downstream gas scrub, in which case the separated isocyanate would be combined with the isocyanate recovered from quench 12 in stream 106. The preparation of the pure isocyanate is preferably carried out subsequently by distillative work-up of the stream (ii-2), carried in stream 106, which as noted above may optionally include the additional isocyanate from the gas scrub.

In step (iii), shown in FIG. 1 in fractionation step 13, the hydrogen chloride and phosgene present in the gas mixture (ii-1), shown as stream 105 which is combined with stream 115 as explained below, to form stream 117, are separated to give a liquid phosgene-containing stream (iii-1), shown as stream 107, and a gaseous stream (iii-2), shown as stream 108, containing hydrogen chloride.

The gas mixture entering the fractionation in step (iii) generally contains from 1 to 50% by mass of HCl, preferably from 5 to 45% by mass of HCl, particularly preferably from 10 to 40% by mass of HCl and very particularly preferably from 715 to 35% by mass of HCl, based on the mass of the gas mixture. This gas mixture generally contains from 5 to 90% by mass of phosgene, preferably from 15 to 85% by mass of phosgene, particularly preferably from 25 to 80% by mass of phosgene and very particularly preferably from 40 to 75% by mass of phosgene, based on the mass of the gas mixture. The content of solvent in the gas mixture is generally from 0.01 to 60% by mass, preferably from 0.05 to 40% by mass and particularly preferably from 0.1 to 10% by mass, based on the mass of the gas mixture. The solvent can be present in vapor form or as liquid. The gas mixture can additionally contain inert gases in a total amount of generally from 0 to 10% by mass, preferably from 0.0001 to 8% by mass and particularly preferably from 0.001 to 5% by mass, based on the mass of the gas mixture. The gas mixture can generally contain from 0 to 10% by mass, preferably from 0.001 to 7.5% by mass and particularly preferably from 0.05 to 5% by mass, of reaction product, based on the mass of the gas mixture.

The separation in step (iii) can be carried out according to various methods, including absorption in a solvent, partial condensation with a subsequent scrub or a complete or partial condensation with a subsequent distillation or a stripping step. A particularly preferred method of fractionation is an absorption in a solvent. Particular preference is given to carrying out the absorption in the solvent which is also used for the quench in step (ii).

In a particularly preferred embodiment, the absorption is carried out in a sequence of at least two absorption steps, optionally in combination with partial condensation steps, with at least one absorption step being carried out isothermally and at least one absorption step being carried out adiabatically. Very particular preference is given to the first absorption step being carried out isothermally, and the following absorption step being carried out adiabatically. In a particularly preferred embodiment, the same solvent which was used in step (ii) is in each case used for the adiabatic absorption step and for the isothermal absorption step. Preference is also given to the gas leaving the last absorption step being freed of any remaining traces of phosgene and solvent by condensation by cooling by means of a heat exchanger. In a preferred embodiment, the isothermal absorption and subsequent adiabatic absorption are carried out in a single apparatus, such as a single absorption column, with the cooling of the gas stream leaving the absorption particularly preferably also being carried out in the same apparatus. This has the advantage that the number of flanges is reduced thereby, contributing to an increase in safety when handling phosgene. It has the further advantage of energy saving since energy losses in the connecting pipes are minimized by the compact construction in one apparatus.

In a further embodiment, step (iii) is carried out by partial condensation with a subsequent scrub. In this particular embodiment, the gas mixture is firstly partially condensed. The remaining gas stream is introduced from the bottom into an absorption column and scrubbed in countercurrent with the solvent. The heat of absorption is removed by means of external heat exchangers. For this purpose, the liquid can be taken off in its entirety or in part, preferably in its entirety, preferably at various places on the absorption column, and cooled by means of an external cooler.

A further possible embodiment for carrying out step (iii) is the partial or complete condensation of phosgene, subsequently a distillation or stripping step in a column in order to remove the dissolved HCl from the bottom product phosgene and subsequently a scrub of the overhead product HCl obtained in the first step using a solvent for absorption of the phosgene remaining in the gas stream after the condensation. The liquid stream obtained at the bottom of the distillation or stripping step has only a small loading with dissolved HCl and/or inert gases and can be introduced into step (iv).

The above-described process alternatives for carrying out the step (iii) all give a gaseous stream (iii-2), shown as stream 108, and a liquid stream (iii-1) shown as stream 107. The HCl-containing gas stream (iii-2) has a sufficient purity and can generally be processed further without further purification.

In one embodiment of the present invention, the fresh phosgene which has to be introduced in order to replace the phosgene consumed in step (i) is added in step (iii) and thus becomes a constituent of the liquid phosgene-containing stream (iii-1) obtained in this step. There are various possibilities for this. Thus, fresh phosgene can, for example, in the embodiment of step (iii) in which this step comprises absorption in a solvent, be introduced, optionally after liquefaction, into the bottom of the corresponding absorption column.

The gas stream (iii-2) leaving the step (iii) contains essentially HCl and possibly traces of phosgene. Apart from HCl, the stream can additionally contain inert gases and/or solvent and also traces of reaction by-products. The stream contains from 80 to 100% by mass, preferably from 90 to 100% by mass and particularly preferably from 95 to 100% by mass, of HCl, based on the mass of the gas stream (iii-2). This gas stream normally contains not more than 2% by mass of phosgene, preferably not more than 0.4% by mass and particularly preferably not more than 0.2% by mass of phosgene, based on the mass of the gas stream (iii-2). To achieve optimization in terms of energy, it can be preferable to permit at least 1 ppm by mass of phosgene, preferably at least 5 ppm by mass of phosgene, based on the mass of the gas stream (iii-2), with the abovementioned maximum limits for the phosgene content applying in both cases. The gas stream (iii-2) leaving step (iii) is generally under a pressure of from 1.00 to 4.00 bar absolute, preferably from 1.01 to 3.00 bar absolute and particularly preferably from 1.02 to 2.00 bar absolute, at the outlet from the process step. The gas stream obtained from step (iii) generally has a temperature of from −40 to 30° C., preferably from −20 to 20° C. and particularly preferably from −15 to 10° C., at the outlet from the process step. For the purposes of the present invention, the outlet from the process step is the gas exit port of the last apparatus belonging to this process step.

Regardless of the precise configuration of step (iii), the liquid phosgene-containing stream (iii-1) leaving this step contains phosgene together with solvent (solvent which has not been completely separated off in step (ii) and optionally the absorption solvent from step (iii)). Dissolved HCl and/or dissolved inert materials and also possibly dissolved reaction by-products may also still be present. The stream (iii-1) contains from 20 to 90% by mass, preferably from 25 to 85% by mass and particularly preferably from 30 to 70% by mass, of phosgene, based on the mass of the liquid phosgene-containing stream (iii-1). In addition, this stream contains from 10 to 80% by mass, preferably from 15 to 75% by mass and in particular preferably from 30 to 70% by mass, of solvent, based on the mass of the liquid phosgene-containing stream (iii-1). Furthermore, this liquid stream (iii-1) can contain from 0 to 5% by mass, preferably from 0.1 to 3.5% by mass and particularly preferably from 0.5 to 2.5% by mass, of dissolved hydrogen chloride, based on the weight of the liquid phosgene-containing stream (iii-1).

The liquid phosgene-containing stream (iii-1) exiting from step (iii) generally has a temperature of from −40 to 20° C., preferably from −25 to 15° C. and particularly preferably from −20 to 10° C. This stream is generally under a pressure of from 1.00 to 4.00 bar absolute, preferably from 1.01 to 3.00 bar absolute and particularly preferably from 1.02 to 2.00 bar absolute, at the outlet from the process step. For the purposes of the present invention, the outlet from the process step for the liquid phosgene-containing stream is the liquid exit port from the apparatus(es) belonging to this process step. The pressure measured there is caused by the hydrostatic pressure of the liquid column in the apparatus(es).

This stream (iii-1) may then optionally be partially vaporized in a vaporization step (not shown). This partial vaporization of the stream (iii-1) can, for example, be effected by:
- use of a regulated prevaporizer (i.e. introduction of heat at approximately the pressure of the distillation column of step (iv), formation of a vapor phase as a result),
- regulated flash evaporation (partial vaporization by lowering of the pressure) or
- regulated superheating of the liquid feed stream (iii-1) under superatmospheric pressure (i.e. heating the liquid feed under superatmospheric pressure to a temperature which is above the boiling point of the mixture at the pressure of the distillation column in step (iv)).

The preheating and partial vaporization reduces the energy costs by the introduction of heat at the bottom of the distillation column in step (iv) to a high temperature level being partly replaced by introduction of heat at a lower temperature level in the feed to the column.

The preheating and partial vaporization can optionally also be carried out in a plurality of steps (i.e. by means of a plurality of apparatuses and/or a plurality of heating media).

The preheating and partial vaporization can, particularly because of the low to moderate temperature level, optionally also be carried out by heat integration with suitable process streams and/or waste heat streams (condensate, low-pressure steam) and thus allows particularly energy-efficient operation of the plant, in contrast to the prior art independently of the configuration of the distillation column of step (iv) with or without enrichment section.

If the preheating and partial vaporization is carried out in a plurality of steps, it is not necessary for all steps to be regulated in respect of heat transfer, which frequently assists heat integration by little reverse effect on other process steps and thereby leads to more robust operational behavior of the overall process.

When preheating and partial vaporization is carried out in a plurality of steps and optionally by means of various heating media, it is also possible for a plurality of these steps to be integrated in one apparatus. Reduced apparatus volumes and further connections between apparatuses and pipes are advantageous from the safety point of view, especially in the case of phosgene-conveying apparatuses, and lead to lower apparatus costs.

The above-described procedure also makes it possible to regulate the pressure in the distillation column of the subsequent step (iv), the step of production of gaseous recycled phosgene shown as distillation step 14, from which the recovered phosgene is used in the reaction of step (v), by varying the amount of the vapor introduced directly into the mixture to be separated in the distillation column. For the purposes of the present invention, the "pressure in the distillation column of step (iv)" is the pressure measured at the top of the column. The expression "vapor introduced directly into the mixture to be separated in this distillation column" refers here to streams which contain phosgene vapor and come into contact in terms of material with the mixture to be separated in the distillation column, i.e. refers, in particular, to the vapor fraction obtained in step (iii), which may or may not be coming off of the optional vaporization step. In the following, the expression "vapor introduced directly" will also be used for short. A distinction is made between this and heating steam which is introduced via an indirect heating device and is not in contact in terms of material with the mixture to be separated in the distillation column. Also for purposes of the present application, phosgene-containing stream (iii-1), shown as stream 107, may come directly from step (iii), or it may come from the optional vaporization step described above.

Conventional pressure regulating systems for columns use, in the case of overhead product being taken off in vapor form (see Kister: "Distillation Operation" chapter 17.2), either (a) the amount of overhead product taken off itself or (b) the condensation power as manipulated variable, more rarely (c) systems which "breathe" opposite the atmosphere or inert gas or (d) regulation concepts working via the bottom vaporizer. Disadvantages of this procedure of the prior art for the present application would be: (a) the overhead product offtake stream cannot simultaneously be controlled variable and manipulated variable; (b) the use of the condensation power as manipulated variable is not quick enough, in particular in order to make available quickly increasing amounts of phosgene as overhead product stream; the variant (c) is not advantageous because of the phosgene loss and the necessity of introducing inert gas; (d) the use of the bottom vaporizer as manipulated variable is not quick enough (see (b)).

However, a stable column pressure in step (iv) can be regulated particularly well by using an (at least partially) gaseous, phosgene-containing feed stream (the two-phase process product from step (iii)) for producing the gaseous recycle phosgene as manipulated variable of the pressure regulation.

In the present application, the parameters column pressure and amount of phosgene taken off at the top of the distillation column of step (iv) are coupled closely to one another, so that the pressure regulation according to the invention, which influences both parameters in parallel, is particularly effective.

As noted above, fresh phosgene is introduced in step (i). In one embodiment, only fresh phosgene is used in step (i). In another embodiment, the fresh phosgene can be mixed with the gaseous phosgene-containing stream from step (iv) (i.e. the "recycled phosgene") before this stream is fed to the reaction of step (i). In both variants mentioned, fresh phosgene can be fed in unliquefied form, including any inert gases present and any excess carbon monoxide present, from its production directly to the reactor, provided that the desired type of further use of the hydrogen chloride formed in the process permits this in respect of its purity.

In an embodiment of the present invention, recycled phosgene, shown in FIG. 1 as stream 110, is taken off the top of distillation column 14 and is fed into reactor 15. In an embodiment, only recycled phosgene, and not fresh phosgene, is used as the phosgene in reactor 15. As noted above, in another embodiment recycled phosgene may be combined with fresh phosgene and added to reactor 11. Likewise, fresh phosgene may also be added to reactor 15. Stream 110 may optionally include inert or carrier gases, in addition to any other gases from distillation step 14. In one embodiment, the concentration of hydrogen chloride (HCl) in stream 110 is greater than the concentration of HCl in stream 102. In another embodiment, the HCl concentration in stream 110 entering reactor 15 is preferably between 1% and 5%.

Referring again to FIG. 1, a second amine is carried through stream 111 to be reacted with recycled phosgene in stream 110 in reactor 15, to create a second process product in stream 113. The second amine may be the same or a different amine as the ones described above in association with reactor 11.

After the phosgenation reaction has occurred in reactor 15, the second process product, which comprises the isocyanate formed, phosgene and hydrogen chloride, is carried through stream 113 to quench 16, where the second process product is treated with a solvent, which stops any further reaction and separates the isocyanate formed from the gaseous phosgene and hydrogen chloride.

As shown in FIG. 1, the second process product which continuously leaves reactor 15 is condensed with an inert solvent in quench 16. The condensation is preferably carried out by the process product leaving reactor 15 being conveyed in stream 113 into quench 16 into which one or more suitable solvent streams, or quenching liquids, comprising a second solvent are sprayed, shown as stream 114. In a preferred embodiment, the first solvent and the second solvent are the same solvent. Rapid cooling of the gas mixtures without the use of cold surfaces can be carried out thereby, as described in EP-A-1 403 248.

The treatment with solvent is carried out at a temperature which is below the boiling point of the second isocyanate and above the decomposition temperature of the corresponding carbamoyl chloride, so as to give a gaseous stream (vi-1) containing hydrogen chloride and unreacted phosgene, shown in stream 115 and a liquid stream (vi-2) containing solvent and isocyanate, shown in stream 116. As noted above, stream 115 is combined with stream 105 to form stream 117, which in turn is fed into fractionation step 13. Alternatively, stream 105 and stream 115 may each be fed into fractionation step 13, without being combined first.

It is likewise conceivable for a portion of the fresh phosgene to be introduced in liquid form, for example as a condensed liquid or as a solution in a solvent, preferably as a solution in the solvent used in quench 12 or quench 16, or preferably in pure form, into the distillation column of step (iv), e.g. into the bottom of this column, with the bottom of the column then performing the function of a phosgene vaporizer. However, in a preferred embodiment, liquid fresh phosgene is introduced directly at the top of this column, so that the liquid fresh phosgene can partly replace the function of the runback. If, although possible in principle, an overhead condenser of the distillation column of step (iv) is not to be omitted, fresh phosgene can also be fed to this overhead condenser in liquid form as runback to the distillation column.

In a preferred embodiment of the process of the invention, variation of the amount of the vapor fed to the distillation column of step (iv) is carried out by variation of the proportion of vapor in the two-phase process product produced in step (iii), which may include the vaporization step. This is preferably effected by varying the temperature of the two-phase process product from step (iii): the higher this temperature, the greater is the proportion of vapor and vice versa. The temperature of the two-phase process product can, in the case of steam heating, be set by, for example, suitable regulation of the heating steam.

In another embodiment of the process of the invention, the distillation column of step (iv) is supplied with gaseous fresh phosgene in addition to the two-phase process product from step (iii), i.e. the vapor introduced directly into the distillation column comprises the vapor fraction of the two-phase process product from step (iii) and fresh phosgene vapor provided separately. It is not necessary to use a fully gaseous phosgene stream for this purpose; rather, it is also possible to introduce a further two-phase stream (i.e. a stream containing liquid and gaseous fractions) into the distillation column of step (iv). In this embodiment, too, variation of the amount of the vapor fed to the distillation column of step (iv) can be carried out by variation of the proportion of vapor in the two-phase process product produced in step (iii). However, it can also be carried out by variation of the proportion of vapor in the further stream containing phosgene vapor (if the stream is not already entirely present in vapor form but instead has a variable proportion of liquid). A combination of the two measures is also conceivable.

In this embodiment in particular (but not restricted to this embodiment), it can be advantageous to carry out the variation of the amount of the vapor introduced directly into the distillation column of step (iv) by variation of the total amount (i.e. the sum of liquid fraction and gaseous fraction) of two-phase process product from step (iii) fed to this column and/or by variation of the total amount of separately provided, optionally two-phase, stream containing phosgene vapor which is fed to this column. Here, the proportion of vapor, expressed as proportion by mass of the total stream from step (iii), in the two-phase process product produced in step (iii) is preferably kept essentially constant. "Essentially constant" here means that a proportion of vapor which has been set fluctuates by not more than an absolute value corresponding to 3% of the intended value of the proportion of vapor. If the variation of the total amount of an above-described additionally introduced, optionally two-phase, stream containing phosgene vapor is additionally or exclusively used for the regulating task, the proportion of vapor in this is preferably kept essentially constant. "Essentially constant" here means that a proportion of vapor which has been set fluctuates by not more than an absolute value corresponding to 3% of the intended value for the proportion of vapor.

This embodiment allows the gaseous fresh phosgene also to be used as pressure-regulating feed stream. The regulation of the pressure by means of the gaseous feed to the distillation column of step (iv) enables the overhead condenser as regulating device and the enrichment section to be dispensed with. A relatively high proportion of solvent in the recycle phosgene, compared to that disclosed in specific working examples in the prior art, is intentionally accepted and has not been found to be disadvantageous in practice (in respect of reaction yield, by-products, etc.). The proportion of solvent in the recycle phosgene can be set in a targeted manner by means of the feed temperature to the distillation column of step (iv). Tracking of the feed temperature enables the proportion of solvent in the recycle phosgene to be kept constant even in the case of altered feed parameters (composition, pressure), which represents an advantage over the prior art (for example an unregulated stripping column). A higher feed temperature leads, inter alia, to an increased proportion of solvent in the recycle phosgene, but on the other hand also reduces the energy costs by a higher heat integration contribution and waste heat utilization for feed heating and by a reduced energy consumption for heating the recycle phosgene stream. A feed temperature (i.e. the temperature of the two-phase process product from step (iii) on introduction into the distillation column of step (iv)) of from 20° C. to 150° C., preferably from 30° C. to 120° C., particularly preferably from 60° C. to 110° C., and a proportion of solvent in the gaseous phosgene-containing stream from step (v) of from 1.0% by mass to 15% by mass, preferably from 2.5% by mass to 10% by mass, particularly preferably from 3.0% by mass to 7.5% by mass, at a pressure in the distillation column of step (iv) of from 10 mbar above to 1500 mbar above ambient pressure (measured at the top of the column) have been found to be particularly advantageous.

The work-up of the liquid stream (ii-2), shown as stream 106, containing the first solvent and the first isocyanate which is obtained in step (ii) in order to recover the desired first isocyanate can be carried out by several known methods, including distillation. Likewise, liquid stream (vi-2), shown as stream 116, containing the second solvent and the second isocyanate which is obtained in step (vi), may also be further processed in order to recover the desired second isocyanate using a known method such as distillation.

Figure 2:
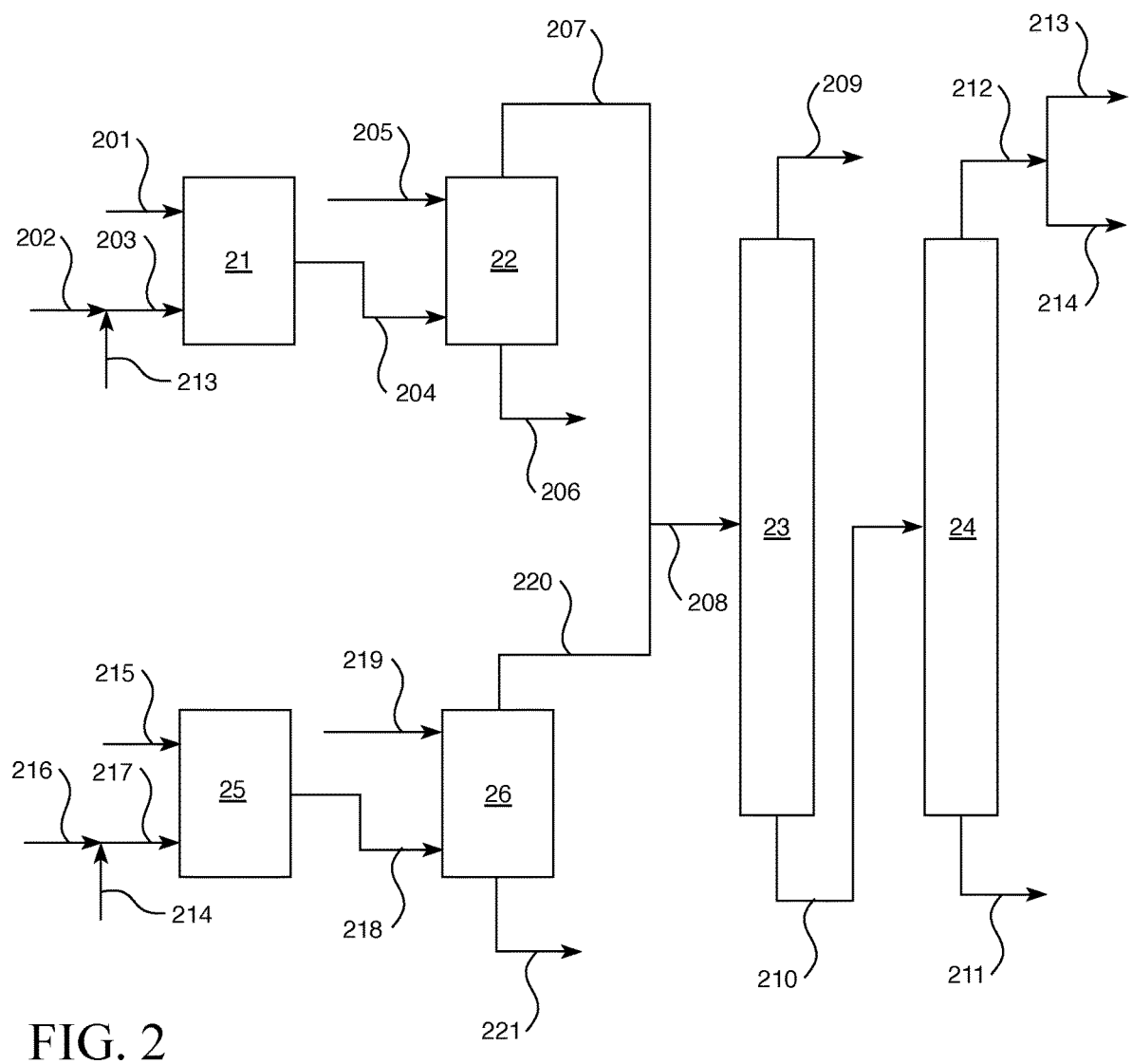
FIG. 2 is a process flow diagram of a continuous process of another embodiment of the present invention.

In another embodiment as shown in FIG. 2, a first amine is carried through stream 201 to be reacted with freshly generated phosgene in stream 202, which is first combined with recycled phosgene in stream 213 to form stream 203 in reactor 21, to create a first process product in stream 204. Stream 203 may optional comprise inert or carrier gases. The concentration of hydrogen chloride (HCl) in stream 203 is between 0.0% and 1%, preferably between 0.0% and 0.1%, and in another embodiment preferably between greater than 0.0% and 1%, or between greater than 0.0% and 0.1%.

After the phosgenation reaction has occurred in reactor 21, the first process product, which comprises the isocyanate formed, phosgene and hydrogen chloride, is carried through stream 204 to quench 22, where the first process product is treated with a solvent, which stops any further reaction and separates the isocyanate formed from the gaseous phosgene and hydrogen chloride. The first process product which continuously leaves reactor 21 is condensed with an inert solvent in quench 22. The condensation is preferably carried out by the process product leaving reactor 21 being conveyed in stream 204 into quench 22 into which one or more suitable solvent streams, or quenching liquids, comprising a first solvent are sprayed, shown as stream 205.

The treatment with solvent is carried out as described above, in association with the quench step (ii).

The gas mixture (ii-1), shown as stream 207, may be optionally treated to remove residual isocyanate by means of a suitable scrubbing liquid in a downstream gas scrub, in which case the separated isocyanate would be combined with the isocyanate recovered from quench 22 in stream 206. The preparation of the pure isocyanate is preferably carried out subsequently by distillative work-up of the stream (ii-2), carried in stream 206, which as noted above may optionally include the additional isocyanate from the gas scrub.

In step (iii), shown in FIG. 2 in fractionation step 23, the hydrogen chloride and phosgene present in the gas mixture (ii-1), shown as stream 207 which is combined with stream 220 as explained below, to form stream 208, are separated to give a liquid phosgene-containing stream (iii-1), shown as stream 210, and a gaseous stream (iii-2), shown as stream 209, containing hydrogen chloride. In another embodiment, streams 207 and 220 go directly into fractionation step 23, without being combined first.

In an embodiment of the present invention, recycled phosgene, shown in FIG. 2 as stream 212, is taken off the top of distillation column 24 and is fed into reactor 25. In the embodiment shown in FIG. 2, stream 212 is split into streams 213 and 214. Streams 213 and 214 may each comprise anywhere from 0-100 wt. % of stream 212, wherein the wt. % of streams 213 and 214 add up to 100 wt. %. Stream 213 is combined with stream 202 to form stream 203. In another embodiment, streams 202 and 213 are fed directly into reactor 21. Stream 214 is combined with stream 216 to form stream 217. In another embodiment, streams 216 and 214 are fed directly into reactor 25. In an embodiment, only recycled phosgene, and not fresh phosgene, is used as the phosgene in reactor 25. In this embodiment, stream 214 is fed directly into reactor 25. Stream 216 composes fresh phosgene that may be added to reactor 25. Stream 214 may optionally include inert or carrier gases, in addition to any other gases from distillation step 24. In one embodiment, the concentration of hydrogen chloride (HCl) in stream 217 is greater than the concentration of HCl in stream 203. In another embodiment, the HCl concentration in stream 217 entering reactor 25 is preferably between 1% and 5%.

Referring again to FIG. 2, a second amine is carried through stream 215 to be reacted with recycled phosgene in stream 217 in reactor 25, to create a second process product in stream 218. After the phosgenation reaction has occurred in reactor 25, the second process product, which comprises the isocyanate formed, phosgene and hydrogen chloride, is carried through stream 218 to quench 26, where the second process product is treated with a solvent from stream 219, which stops any further reaction and separates the isocyanate formed from the gaseous phosgene and hydrogen chloride.

As shown in FIG. 2, the second process product which continuously leaves reactor 25 is condensed with an inert solvent in quench 26. The condensation is preferably carried out by the process product leaving reactor 25 being conveyed in stream 218 into quench 26 into which one or more suitable solvent streams, or quenching liquids, comprising a first solvent are sprayed, shown as stream 219.

The treatment with solvent is carried out at a temperature which is below the boiling point of the second isocyanate and above the decomposition temperature of the corresponding carbamoyl chloride, so as to give a gaseous stream (vi-1) containing hydrogen chloride and unreacted phosgene, shown in stream 220 and a liquid stream (vi-2) containing solvent and isocyanate, shown in stream 221. As noted above, stream 220 is combined with stream 207 to form stream 208, which in turn in fed into fractionation step 23. Alternatively, stream 207 and stream 220 may each be fed into fractionation step 23, without being combined first.

By creating a process for the manufacture of two isocyanates, certain equipment may be used for both processes, such as the fractionation and distillation steps, which makes both processes use less capital and energy. In addition, better use may be made of recycled phosgene, where the purity of hydrogen chloride is not as critical in the manufacture of the second isocyanate, as it is for the first isocyanate. This means, that the phosgene need not be purified as much of its residual hydrogen chloride in order for it to be used in the manufacture of the second isocyanate. As a result, the distillation step may be less capital intensive and may also use less energy, as less "pure" phosgene may be recovered for use. Furthermore, by adjusting the amount of recycled and fresh phosgene is going into the reactor for each isocyanate, one can optimize the amount spent in capital and operating costs for production of both isocyanates.

The following aspects are disclosed:
1. A continuous process for preparing a first isocyanate by gas phase phosgenation of a first amine, and a second isocyanate by gas phase phosgenation of a second amine, comprising:
   (i) reacting the first amine with freshly generated phosgene to obtain a first process product;
   (ii) treating the first process product with a first solvent at a temperature which is below the boiling point of the first isocyanate to give a gaseous stream (ii-1) containing hydrogen chloride and unreacted phosgene and a liquid stream (ii-2) containing the first solvent and the first isocyanate;
   (iii) feeding stream (ii-1) to a distillation column (iii) to give a liquid phosgene-containing stream (iii-1) and a gaseous stream (iii-2) containing hydrogen chloride;
   (iv) introducing stream (iii-1) to a distillation column (iv), from which a gaseous phosgene-containing stream (iv) is taken off at the top;
   (v) reacting the second amine with an excess of phosgene that comprises gaseous phosgene-containing stream (iv) to obtain a second process product;
   (vi) treating the second process product with a second solvent at a temperature which is below the boiling point of the second isocyanate to give a gaseous stream (vi-1) containing hydrogen chloride and unreacted phosgene and a liquid stream (vi-2) containing the second solvent and the second isocyanate;
   (vii) feeding stream (vi-1) to distillation column (iii);
   (viii) working up the liquid stream (ii-2) containing solvent and the first isocyanate to isolate the first isocyanate;
   (ix) working up the liquid stream (vi-2) containing solvent and the second isocyanate to isolate the second isocyanate.
2. A continuous process for preparing a first isocyanate by gas phase phosgenation of a first amine, and a second isocyanate by gas phase phosgenation of a second amine, comprising:
   (i) reacting the first amine with an excess of phosgene having a concentration of hydrogen chloride of HCl-1 to obtain a first process product;
   (ii) treating the first process product with a first solvent at a temperature which is below the boiling point of the first isocyanate to give a gaseous stream (ii-1) containing hydrogen chloride and unreacted phosgene and a liquid stream (ii-2) containing the first solvent and the first isocyanate;
   (iii) feeding stream (ii-1) to a distillation column (iii) to give a liquid phosgene-containing stream (iii-1) and a gaseous stream (iii-2) containing hydrogen chloride;
   (iv) introducing stream (iii-1) to a distillation column, from which a gaseous phosgene-containing stream (iv) is taken off at the top;
   (v) splitting the gaseous phosgene-containing stream (iv) into stream (v-1) and stream (v-2);
   (vi) recirculating stream (v-1) to step (i);
   (vii) working up the liquid stream (ii-2) containing the first solvent and the first isocyanate to isolate the first isocyanate;
   (viii) reacting the second amine with an excess of phosgene having a concentration of hydrogen chloride of HCl-2 to obtain a second process product;
   (ix) treating the second process product with a second solvent at a temperature which is below the boiling point of the second isocyanate to give a gaseous stream (ix-1) containing hydrogen chloride and unreacted phosgene and a liquid stream (ix-2) containing the second solvent and the second isocyanate;
   (x) feeding stream (ix-1) to distillation column (iii);
   (xi) recirculating stream (v-2) to step (viii);
   (xii) working up the liquid stream (ix-2) containing the second solvent and the second isocyanate to isolate the second isocyanate,
   wherein the excess of phosgene in step (i) comes at least partially from stream (v-1),
   wherein the excess of phosgene in step (viii) comes at least partially from stream (v-2),
   wherein HCl-2 is greater than HCl-1.
3. The process of aspect 1, wherein the first amine in step (i) is not reacted with any recycled phosgene.
4. The process of any of the proceeding aspects, wherein the first process product has a corresponding carbamoyl chloride and the temperature of the first quench step is above the decomposition temperature of the corresponding carbamoyl chloride.
5. The process of any of the proceeding aspects, wherein the second process product has a corresponding carbamoyl chloride and the temperature of the second quench step is above the decomposition temperature of the corresponding carbamoyl chloride.
6. The process of any of the proceeding aspects, wherein the excess of phosgene reacted with the second amine further comprises freshly generated phosgene.
7. The process of any of the proceeding aspects, wherein the phosgene that is reacted with the first amine has a concentration of hydrogen chloride HCl-1 and the phosgene that is reacted with the second amine has a concentration of hydrogen chloride HCl-2, and wherein HCl-2 is greater than HCl-1.
8. The process of any of the proceeding aspects, wherein HCl-1 is between 0.0% and 1% by weight, preferably between 0.0% and 0.1% by weight.
9. The process of any of the proceeding aspects, wherein HCl-2 is between 1% and 5% by weight.
10. The process of any of the proceeding aspects, wherein the first solvent is the same as the second solvent.

The invention claimed is:
1. A continuous process for preparing a first isocyanate by gas phase phosgenation of a first amine, and a second isocyanate by gas phase phosgenation of a second amine, comprising:
   (i) reacting the first amine with freshly generated phosgene to obtain a first process product;
   (ii) treating the first process product with a first solvent at a temperature which is below the boiling point of the first isocyanate to give a gaseous stream (ii-1) containing hydrogen chloride and unreacted phosgene and a liquid stream (ii-2) containing the first solvent and the first isocyanate;
   (iii) feeding stream (ii-1) to a distillation column (iii) to give a liquid phosgene-containing stream (iii-1) and a gaseous stream (iii-2) containing hydrogen chloride;
   (iv) introducing stream (iii-1) to a distillation column (iv), from which a gaseous phosgene-containing stream (iv) is taken off at the top;
   (v) reacting the second amine with an excess of phosgene that comprises gaseous phosgene-containing stream (iv) to obtain a second process product;
   (vi) treating the second process product with a second solvent at a temperature which is below the boiling point of the second isocyanate to give a gaseous stream

(vi-1) containing hydrogen chloride and unreacted phosgene and a liquid stream (vi-2) containing the second solvent and the second isocyanate;

(vii) feeding stream (vi-1) to distillation column (iii);

(viii) working up the liquid stream (ii-2) containing solvent and the first isocyanate to isolate the first isocyanate;

(ix) working up the liquid stream (vi-2) containing solvent and the second isocyanate to isolate the second isocyanate;

wherein the phosgene that is reacted in step (i) has a concentration of hydrogen chloride HCl-1 and the phosgene that is reacted in step (v) has a concentration of hydrogen chloride HCl-2, wherein HCl-2 is greater than HCl-1, and wherein HCl-1 is between 0.0% and 0.1% by weight or HCl-2 is between 1% and 5% by weight.

2. The process of claim 1, wherein the first amine in step (i) is not reacted with any recycled phosgene.

3. The process of claim 1, wherein the first process product has a corresponding carbamoyl chloride and the temperature of step (ii) is above the decomposition temperature of the corresponding carbamoyl chloride.

4. The process of claim 1, wherein the second process product has a corresponding carbamoyl chloride and the temperature of step (vi) is above the decomposition temperature of the corresponding carbamoyl chloride.

5. The process of claim 1, wherein the excess of phosgene in step (v) further comprises freshly generated phosgene.

6. The process of claim 5, wherein HCl-1 is between 0.0% and 0.1% by weight.

7. The process of claim 5, wherein HCl-2 is between 1% and 5% by weight.

8. The process of claim 1, wherein the first solvent is the same as the second solvent.

9. A continuous process for preparing a first isocyanate by gas phase phosgenation of a first amine, and a second isocyanate by gas phase phosgenation of a second amine, comprising:

(i) reacting the first amine with an excess of phosgene having a concentration of hydrogen chloride of HCl-1 to obtain a first process product;

(ii) treating the first process product with a first solvent at a temperature which is below the boiling point of the first isocyanate to give a gaseous stream (ii-1) containing hydrogen chloride and unreacted phosgene and a liquid stream (ii-2) containing the first solvent and the first isocyanate;

(iii) feeding stream (ii-1) to a distillation column (iii) to give a liquid phosgene-containing stream (iii-1) and a gaseous stream (iii-2) containing hydrogen chloride;

(iv) introducing stream (iii-1) to a distillation column, from which a gaseous phosgene-containing stream (iv) is taken off at the top;

(v) splitting the gaseous phosgene-containing stream (iv) into stream (v-1) and stream (v-2);

(vi) recirculating stream (v-1) to step (i);

(vii) working up the liquid stream (ii-2) containing the first solvent and the first isocyanate to isolate the first isocyanate;

(viii) reacting the second amine with an excess of phosgene having a concentration of hydrogen chloride of HCl-2 to obtain a second process product;

(ix) treating the second process product with a second solvent at a temperature which is below the boiling point of the second isocyanate to give a gaseous stream (ix-1) containing hydrogen chloride and unreacted phosgene and a liquid stream (ix-2) containing the second solvent and the second isocyanate;

(x) feeding stream (ix-1) to distillation column (iii);

(xi) recirculating stream (v-2) to step (viii);

(xii) working up the liquid stream (ix-2) containing the second solvent and the second isocyanate to isolate the second isocyanate, wherein the excess of phosgene in step (i) comes at least partially from stream (v-1), wherein the excess of phosgene in step (viii) comes at least partially from stream (v-2), wherein HCl-2 is greater than HCl-1, and wherein HCl-1 is between 0.0% and 0.1% by weight or HCl-2 is between 1% and 5% by weight.

10. The process of claim 9, wherein the excess of phosgene in step (i) comprises freshly generated phosgene.

11. The process of claim 9, wherein the first process product has a corresponding carbamoyl chloride and the temperature of step (ii) is above the decomposition temperature of the corresponding carbamoyl chloride.

12. The process of claim 9, wherein the second process product has a corresponding carbamoyl chloride and the temperature of step (ix) is above the decomposition temperature of the corresponding carbamoyl chloride.

13. The process of claim 9, wherein the excess of phosgene in step (viii) comprises freshly generated phosgene.

14. The process of claim 9, wherein HCl-1 is between 0.0% and 0.1% by weight.

15. The process of claim 9, wherein HCl-2 is between 1% and 5% by weight.

16. The process of claim 9, wherein the first solvent is the same as the second solvent.

* * * * *